United States Patent [19]

Jan

[11] 4,266,011
[45] May 5, 1981

[54] PROCESS FOR THE PRODUCTION OF COLORED PHOTOGRAPHIC IMAGES BY THE SILVER DYE-BLEACH PROCESS

[75] Inventor: Gerald Jan, Marly, Switzerland

[73] Assignee: Ciba-Geigy AG, Basel, Switzerland

[21] Appl. No.: 77,461

[22] Filed: Sep. 20, 1979

[30] Foreign Application Priority Data

Sep. 29, 1978 [CH] Switzerland .................. 10196/78

[51] Int. Cl.³ ............................................. G03C 7/00
[52] U.S. Cl. .................................. 430/392; 430/431;
430/461; 430/462; 430/559
[58] Field of Search ............... 430/392, 431, 462, 17,
430/461, 559

[56] References Cited

U.S. PATENT DOCUMENTS

| | | | |
|---|---|---|---|
| 2,270,118 | 1/1942 | Gaspar | 430/392 |
| 2,627,461 | 2/1953 | Friedman | 430/462 |
| 3,443,947 | 5/1969 | Mory et al. | 430/392 |
| 3,754,918 | 8/1973 | Hunig et al. | 430/462 |
| 4,145,217 | 3/1979 | Jan et al. | 430/392 |

Primary Examiner—J. Travis Brown
Attorney, Agent, or Firm—Sprung, Felfe, Horn, Lynch & Kramer

[57] ABSTRACT

A process for the production of colored photographic images by the silver dye-bleach process by image-wise exposure and subsequent processing by developing the silver image, dye-bleaching and silver bleaching, it being possible, optionally, for the last two steps to be combined, silver fixing and washing, in which process dye-bleaching and/or silver bleaching is carried out in the presence of at least one bleach catalyst of the formula

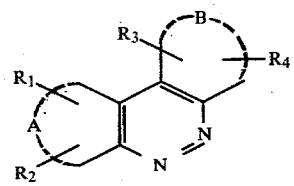

In the formula, A and B are in each case the non-metallic atoms necessary to complete a benzene or pyridine ring, $R_1$ and $R_3$ are each hydrogen, hydroxyl, halogen, alkyl, carboxyl, carbalkoxy, carbalkoxyalkoxy, $-CH_2OH$, $-O(CH_2)_nOH$, $-O(CH_2)_2O(CH_2)_2OH$, $-CH_2Cl$, $-CH_2Br$, $-NR_5R_6$, $-CH_2NR_5R_6$, $-O(CH_2)_nNR_5R_6$, $-CH_2SO_3M$, $-O(CH_2)_nSO_3M$ or $-SO_3M$, $R_2$ and $R_4$ are each hydrogen, hydroxyl, alkyl or alkoxy and $R_5$ and $R_6$ are each hydrogen or alkyl, M is hydrogen, an alkali metal, ammonium or alkylammonium and n is an integer from 2 to 4.

20 Claims, No Drawings

PROCESS FOR THE PRODUCTION OF COLORED PHOTOGRAPHIC IMAGES BY THE SILVER DYE-BLEACH PROCESS

The present invention relates to the use of benzo- or pyrido-[c]-cinnolines or bis-pyridopyridazines as bleach catalysts when processing photographic silver dye-bleach materials.

As is known, the recording material used to produce multi-coloured photographic images by the silver dye-bleach process is a recording material for colour photography which has several silver halide emulsion layers which are arranged one on top of the other and contain bleachable dyes, these layers being light-sensitive to the particular part of the spectrum which is complementary to the colours of these dyes. Image-wise exposure is followed by conventional black-and-white developing and then by a treatment in a dye-bleach bath, in which the dyes are bleached (removed) in proportion to the metallic silver formed during developing. The further treatment steps are silver bleaching, which if desired can also be combined with dye bleaching, and silver fixing and washing. A positive coloured image is obtained. The bleaching baths for dye bleaching and/or silver bleaching contain, as essential components, a strong acid, a silver halide solvent (silver complexing agent), an antioxidant and a bleach catalyst and, if desired, if silver and dye are to be bleached at the same time, an oxidising agent. Diverse categories of, in particular, nitrogen-containing heterocyclic compounds, thus, for example, including cinnolines and pyridazines, have already been disclosed as bleach catalysts.

British Patent No. 711,247 describes cinnolines of the formula

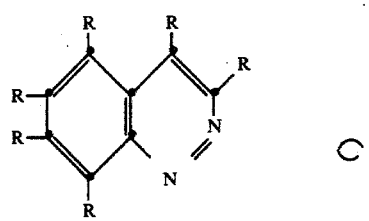

and their use as silver dye-bleach catalysts. The substituents R, which can be identical or different to one another, are, for example, hydrogen, alkyl, alkoxy, aryloxy, aryl or halogen.

Japanese Patent No. 1,089,731 relates to pyridazines of the formula

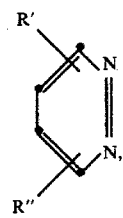

which likewise can be used as silver dye-bleach catalysts. The substituents R' and R", which can be identical or different to one another, are, for example, hydrogen, alkyl, allyl, aryl or acyl.

The cinnolines of the formula (1) and the pyridazines of the formula (2) have only an inadequate bleaching action, since the reversibility of the redox process (with regard to the bleaching mechanism cf., for example, M. Schellenberg and R. Steinmetz, Helv. 52, 431 (1969)), which is necessary for effective bleach catalysts, does not exist or exists to only an inadequate extent in the case of the compounds of the formula (1) and (2). (cf., for example, H. Lund, Acta. Chem. Scand. 21, 2525 (1967) and S. Millefiori, Ann. Chim 59, 15 (1969)). A further disadvantage of these compounds is that they are accessible by synthesis only with difficulty.

The object of the present invention is to provide bleach catalysts for the silver dye-bleach process, which, on the one hand, operate completely reversibly and, on the other hand, present no difficulties in respect of their synthesis, i.e. are readily accessible. It has now been found, surprisingly, that certain benzo- and pyrido-[c]-cinnolines and also bis-pyridopyridazines, in absolute contrast to the cinnolines and pyridazines of the formulae (1) and (2) respectively, are outstandingly effective bleach catalysts for the silver dye-bleach process. The said cinnolines and pyridazines operate completely reversibly, are easy to prepare, are readily soluble in the dye-bleach bath and effect an advantageous gradation.

The present invention therefore relates to a process for the production of coloured photographic images by the silver dye-bleach process by image-wise exposure and subsequent processing by developing the silver image, dye-bleaching and silver bleaching, optionally the last two steps can be combined, silver fixing and washing, which comprises carrying out dye-bleaching and/or silver bleaching in the presence of at least one bleach catalyst of the formula

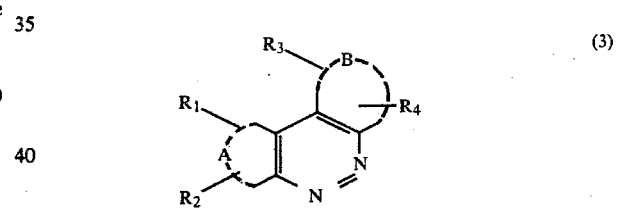

in which A and B are in each case the non-metallic atoms necessary to complete a benzene or pyridine ring, $R_1$ and $R_3$ are each hydrogen, hydroxyl, halogen, alkyl or alkoxy, each having 1 to 4 carbon atoms, carboxyl, carbalkoxy or carbalkoxyalkoxy each having 1 to 4 carbon atoms per alkoxy moiety, $-CH_2OH$, $-O(CH_2)_nOH$, $-O(CH_2)_2O(CH_2)_2OH$, $-CH_2Cl$, $-CH_2Br$, $-NR_5R_6$, $-CH_2NR_5R_6$, $-O(CH_2)_nNR_5R_6$, $-CH_2SO_3M$, $-O(CH_2)_nSO_3M$ or $-SO_3M$, $R_2$ and $R_4$ are each hydrogen, hydroxyl or alkyl or alkoxy, each having 1 to 4 carbon atoms, and $R_5$ and $R_6$ are each hydrogen or alkyl having 1 to 4 carbon atoms, M is hydrogen, an alkali metal, ammonium or alkyl-ammonium having 1 to 4 carbon atoms per alkyl radical and n is an integer from 2 to 4.

The present invention also relates to the aqueous dye-bleach and/or silver dye-bleach preparations for carrying out the process according to the invention, a photographic material for the silver dye-bleach process, which contains a dye-bleach catalyst of the formula (3) in at least one layer, and the coloured photographic images obtained by the process according to the invention. Those compounds of the formula (3) which are novel compounds are a further subject of the present invention.

The substituents $R_1$ and $R_3$ in the compounds of the formula (3) are hydrogen, hydroxyl, halogen, especially fluorine, chlorine and bromine, alkyl or alkoxy each having 1 to 4 carbon atoms, for example methyl, ethyl, propyl, i-propyl, n-butyl, tert.-butyl, methoxy, ethoxy, propoxy or butoxy, or also carboxyl (COOH). As carbalkoxy or carbalkoxyalkoxy each having 1 to 4 carbon atoms per alkoxy moiety, $R_1$ and $R_3$ are, for example, the radicals —COOCH$_3$, —COOC$_2$H$_5$, —COOC$_3$H$_7$, —COOC$_4$H$_9$, —COOCH$_2$OCH$_3$, —COOCH$_2$C-H$_2$OCH$_3$, —COOCH$_2$CH$_2$OC$_2$H$_5$, —COOCH$_2$C-H$_2$OC$_3$H$_7$, —COOCH$_2$CH$_2$OC$_4$H$_9$ or —COO(CH$_2$)$_4$OCH$_3$.

$R_1$ and $R_3$ are also the radicals —CH$_2$OH, —O(CH$_2$)$_n$OH, in which n is 2 to 4, for example —O(CH$_2$)$_2$OH, —O(CH$_2$)$_3$OH or —O(CH$_2$)$_4$OH, or —CH$_2$Cl or —CH$_2$Br.

As —NR$_5$R$_6$, $R_1$ and $R_3$ can be, for example, the following radicals: —NH$_2$, —NHCH$_3$, —NHC$_2$H$_5$, —N(CH$_3$)$_2$, —N(C$_2$H$_5$)$_2$, —NHC$_3$H$_7$, —NHC$_4$H$_9$, —NH(C$_3$H$_7$)$_2$, —N(C$_4$H$_9$)$_2$, —N(CH$_3$)C$_2$H$_5$ or —N(CH$_3$)C$_4$H$_9$.

$R_5$ and $R_6$ in the radicals —CH$_2$NR$_5$R$_6$ and —O(CH$_2$)$_n$NR$_5$R$_6$ can have analogous meanings. In the last-mentioned radical, n is 2 to 4. Finally, if $R_1$ and $R_3$ are the radicals —SO$_3$M, —CH$_2$SO$_3$M or —O(CH$_2$)$_n$SO$_3$M (n is 2 to 4), M can be a hydrogen atom, an alkali metal, especially sodium or potassium, ammonium (NH$_4^\oplus$) or alkylammonium, for example trimethylammonium or triethylammonium. The substituents $R_5$ and $R_6$ are each hydrogen or alkyl having 1 to 4 carbon atoms, for example methyl, ethyl, propyl, i-propyl, n-butyl or tert.-butyl.

Preferred bleach catalysts of the formula (3) are those in which $R_1$ and $R_3$ are each hydrogen, hydroxyl, methyl, ethyl, methoxy, ethoxy, —CH$_2$OH, —O(CH$_2$)$_n$OH, —CH$_2$Cl, —CH$_2$Br, —CH$_2$NR$_6$R$_7$, —O(CH$_2$)$_n$NR$_6$R$_7$, —CH$_2$SO$_3$M, —O(CH$_2$)$_n$SO$_3$M, —SO$_3$M or —NR$_6$R$_7$, $R_2$ and $R_4$ are each hydrogen, hydroxyl, methyl, ethyl, methoxy or ethoxy and $R_6$ and $R_7$ are each hydrogen, methyl or ethyl and A, B, M and n are as defined.

Further bleach catalysts of the formula (3) which are particularly valuable are those in which $R_1$ and $R_3$ are each hydrogen, hydroxyl, methyl, methoxy, —CH$_2$OH, —O(CH$_2$)$_n$OH, —CH$_2$NR$_8$R$_9$, —O(CH$_2$)$_n$NR$_8$R$_9$, —NR$_8$R$_9$, —SO$_3$M, —CH$_2$SO$_3$M or —O(CH$_2$)$_n$SO$_3$M, $R_2$ and $R_4$ are each hydrogen, hydroxyl, methyl or methoxy and $R_8$ and $R_9$ are each hydrogen or methyl and A, B, M and n are as defined.

If the bleach catalysts of the formula (3) are benzo-[c]-cinnolines, these have, for example, the formula

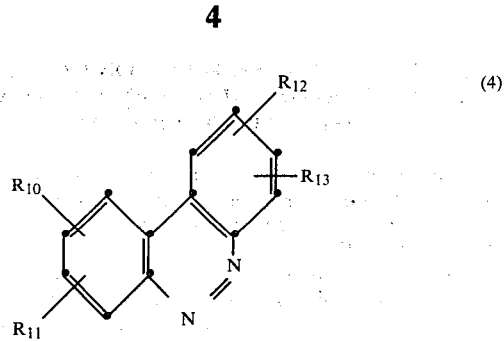

in which $R_1$, $R_2$, $R_3$ and $R_4$ are as defined.

Preferred benzo-[c]-cinnolines of the formula (4) are those of the formula

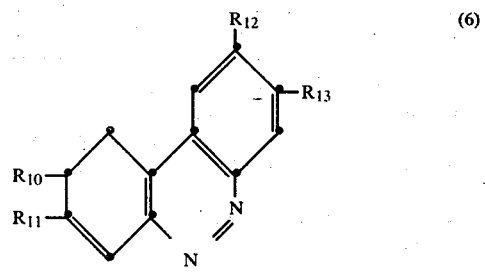

in which $R_{10}$ and $R_{12}$ are each hydrogen, hydroxyl, methyl, methoxy, hydroxymethyl, —O(CH$_2$)$_2$OH, —O(CH$_2$)$_3$OH, —NH$_2$, —N(CH$_3$)$_2$, —SO$_3$M, —CH$_2$SO$_3$M or —O(CH$_2$)$_n$SO$_3$M and $R_{11}$ and $R_{13}$ are each hydrogen, hydroxyl, methyl or methoxy, n is an integer from 2 to 4 and M is hydrogen, an alkali metal, ammonium or alkylammonium having 1 to 4 carbon atoms per alkyl radical.

The compounds of the formula (5) are preferably substituted in the 2/3 and 8/9 positions and therefore have the formulae

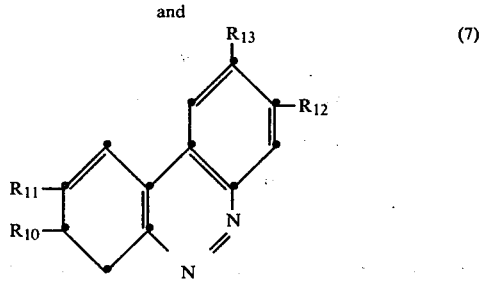

and

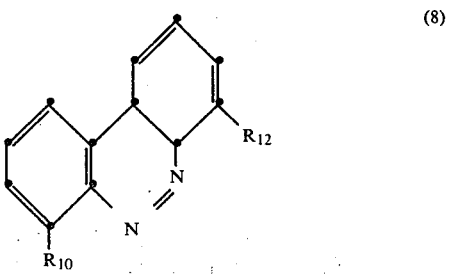

in which $R_{10}$, $R_{11}$, $R_{12}$ and $R_{13}$ are as defined.

Further bleach catalysts which are very suitable are benzo-[c]-cinnolines of the formula (5) which have the formula

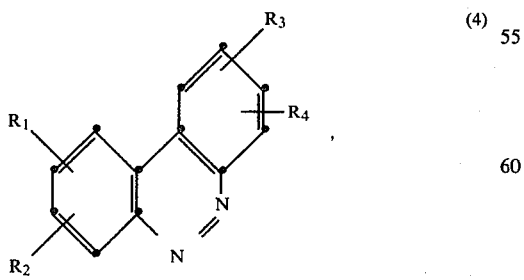

in which $R_{10}$ and $R_{12}$ are as defined.

Particularly suitable pyrido-[c]-cinnolines have the formulae

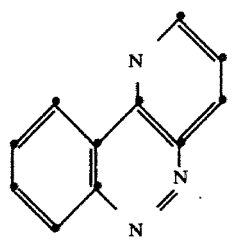 (9)

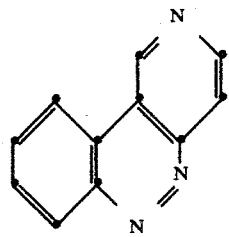 (10)

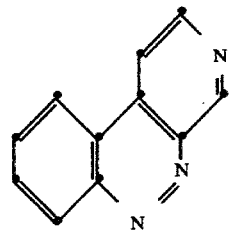 (11)

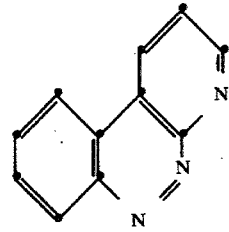 (12)

whilst the preferred bis-pyridopyridazines can be represented, for example, by the formulae

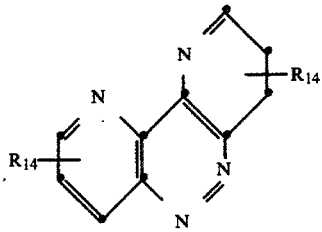 (13)

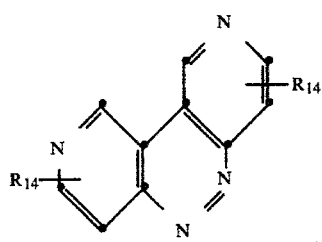 (14)

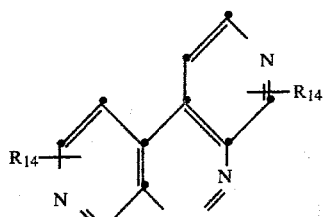 (15)

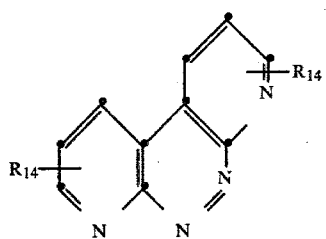 (16)

in which $R_{14}$ is hydrogen or methyl.

Some of the compounds of the formula (3) are known but some of them are novel compounds which can be represented by the following formula

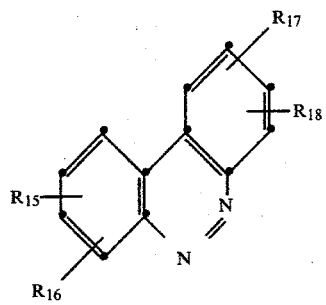 (17)

and in which $R_{15}$ and $R_{17}$ are each hydrogen or alkyl or alkoxy, each having 1 to 4 carbon atoms, $R_{16}$ is hydroxyl, —$CH_2OH$, —$O(CH_2)_nOH$, —$O(CH_2)_2O(CH_2)_2OH$, —$CH_2NR_5R_6$, —$O(CH_2)_nNR_5R_6$, —$CH_2SO_3M$, —$O(CH_2)_nSO_3M$ or —$SO_3M$ and $R_{18}$ is —$CH_2OH$, —$O(CH_2)_nOH$, —$O(CH_2)_2O(CH_2)_2OH$, —$NR_5R_6$, —$CH_2NR_5R_6$, —$O(CH_2)_nNR_5R_6$, —$CH_2SO_3M$, —$O(CH_2)_nSO_3M$ or —$SO_3M$, alkoxy having 1 to 4 carbon atoms or also—if $R_{16}$ is not hydroxyl—hydrogen or alkyl having 1 to 4 carbon atoms, $R_5$ and $R_6$ are each hydrogen or alkyl having 1 to 4 carbon atoms, M is hydrogen, an alkali metal, ammonium or alkylammonium having 1 to 4 carbon atoms per alkyl radical and n is an integer from 2 to 4.

Preferred representatives of the compounds of the formula (17) can be defined by the formulae (18) and (19)

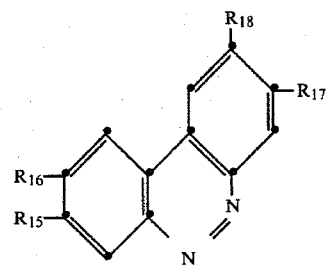 (18)

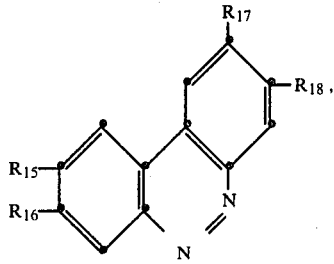

in which $R_{15}$, $R_{16}$, $R_{17}$ and $R_{18}$ are as defined.

Further compounds which are particularly suitable for the process according to the invention are the compounds (benzo-[c]-cinnolines) of the formula

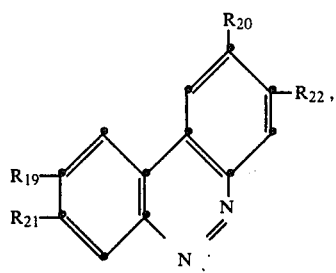

in which $R_{21}$ and $R_{22}$ are each hydrogen, methyl or methoxy, $R_{19}$ is hydroxyl, $-CH_2OH$, $-O(CH_2)_nOH$, $-O(CH_2)_nNR_6R_7$, $-O(CH_2)_nSO_3M$ or $-SO_3M$, $R_{20}$ is $-CH_2OH$, $-O(CH_2)_nOH$, $-NR_6R_7$, $-O(CH_2)_nSO_3M$, $-SO_3M$, $-OCH_3$ or $-OC_2H_5$ or also—if $R_{19}$ is not hydroxyl—hydrogen or methyl, $R_6$ and $R_7$ are each hydrogen, methyl or ethyl, M is hydrogen, an alkali metal, ammonium or alkylammonium having 1 to 4 carbon atoms per alkyl radical and n is an integer from 2 to 4.

Particularly valuable benzo-[c]-cinnolines have the formula

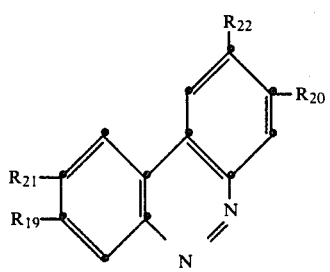

in which $R_{15}$, $R_{17}$, $R_{19}$ and $R_{20}$ are as defined.

The compounds of the formulae (3) to (21) are advantageously prepared in a manner known per se, by reductive cyclisation (reduction/condensation) of 2,2'-dinitrodiphenyl or of corresponding dinitro-2,2'-dipyridyl compounds and, if desired, subsequent hydrolysis or alkylation of the primary reaction products.

In some cases, the primary products from the reductive cyclisation are subjected to further modification, such as, for example, free radical bromination or additional reduction reactions [$-COOR' \rightarrow CH_2OH$]. (cf. N. J. Leonard, Chem. Rev. 37, 269 (1945); J. C. E. Simpson, Condensed Pyridazine and Pyrazine Rings in A. Weissberger, The Chemistry of Heterocyclic Compounds, J. Wiley & Sons, New York 1953, 52 et seq.; T. L. Jacobs, Cinnolines and Related Compounds in R. C. Elderfield, Heterocyclic Compounds Volume 6, J. Wiley & Sons, New York 1957, 173 et seq.). Benzo-[c]-cinnolines can also be prepared from 2,2-diaminobiphenyl derivatives by oxidation (cf. J. F. Corbett and P. F. Holt, J. Chem. Soc. 1961, 3,695 et seq.; J. F. Corbett, P. F. Holt, A. N. Hughes and Mrs. M. Vickery, J. chem. Soc. 1962, 1,812 et seq.; and U.S. Pat. No. 3,087,929). Benzo-[c]-cinnolines can also be prepared from azobenzene compounds by photocatalysed cyclodehydrogenation in the presence of Lewis acids (cf. G. M. Badger, K. J. Drewer and G. E. Lewis, Austr. J. Chem. 16, 1,042 et seq. (1963); ibid. 17, 1,036 et seq. (1964); ibid. 18, 1,639 et seq. (1965); and V. N. R. Pillai and E. Purushothaman, Current Science 46, 381 (1977)). 3-Hydroxy-benzo-[c]-cinnoline derivatives are obtained, for example, from 2-nitrobenzenesulpho-3-hydroxyanilide by heating in an alkaline solution (German Offenlegungsschrift No. 2,118,491).

Suitable starting materials for the syntheses mentioned are, for example, the compounds listed below:

2,2'-Dinitro-biphenyl derivatives

Bis-4,4'-(hydroxymethyl)-2,2'-dinitro-biphenyl, disodium 2,2'-dinitro-biphenyl-4,4'-disulphonate, dipotassium 2,2'-dinitro-biphenyl-4,4'-disulphonate, the disodium salt of 2,2-dinitro-bis-4,4'-(sulphomethyl)-biphenyl, bis-4,4'-(2-hydroxyethoxy)-2,2-dinitro-biphenyl, bis-4,4'-(3-hydroxypropoxy)-2,2'-dinitro-biphenyl, bis-4,4'-(4-hydroxy-1-butoxy)-2,2'-dinitro-biphenyl, bis-4,4'-(N,N-dimethylaminomethyl)-2,2'-dinitro-biphenyl, bis-4,4'-(aminomethyl)-2,2'-dinitrobiphenyl, bis-4,4'-[2-(N,N-dimethylamino)-ethoxy]-2,2,2-dinitro-biphenyl, bis-4,4'-[3-(N,N-dimethylamino)propoxy]-2,2'-dinitro-biphenyl, bis-4,4'-[4-(N,N-dimethylamino)-1-butoxy]-2,2'-dinitro-biphenyl, the disodium salt of 2,2'-dinitro-bis-4,4'-(2-sulphoethoxy)biphenyl, the disodium salt of 2,2'-dinitro-bis-4,4'-(3-sulphopropoxy)-biphenyl and the disodium salt of 2,2'-dinitro-bis-4,4'-(4-sulpho-1-butoxy)-biphenyl.

Benzo-[c]-cinnolines (for hydrolysis of methyl ethers)

3,8-Dimethoxy-benzo-[c]-cinnoline, 2,9-dimethoxy-benzo-[c]-cinnoline and 4,7-dimethoxy-benzo-[c]-cinnoline.

Benzo-[c]-cinnolines (for alkylation)

3-Hydroxy-benzo-[c]-cinnoline, 3,8-dihydroxy-benzo-[c]-cinnoline, 2,9-dihydroxy-benzo-[c]-cinnoline, 4,7-dihydroxy-benzo-[c]-cinnoline, 2-hydroxy-benzo-[c]-cinnoline, 4-hydroxy-benzo-[c]-cinnoline, 3-hydroxy-2-methyl-benzo-[c]-cinnoline, 3-hydroxy-8-methoxy-benzo-[c]-cinnoline, 2-hydroxy-9-methoxy-benzo-[c]-cinnoline and 3-hydroxy-9-methoxy-benzo-[c]-cinnoline.

Benzo-[c]-cinnolines (for diverse chemical reactions)

Benzo-[c]-cinnoline-3,8-dicarboxylic acid, dimethyl benzo-[c]-cinnoline-3,8-dicarboxylate, diethyl benzo-[c]-cinnoline-3,8-dicarboxylate, bis-(2-methoxyethyl) benzo-[c]-cinnoline-3,8-dicarboxylate and 3,8-dimethyl-benzo-[c]-cinnoline.

Alkylating agents

Sodium 2-bromoethanesulphonate, sodium 2-chloroethanesulphonate, sodium vinylsulphonate, propanesultone, butanesultone, N-(2-bromoethyl)-phthalimide, N-(3-bromopropyl)-phthalimide, N-(4-bromo-1-butyl)-phthalimide, 2-(2-bromoethyl)-tetrahydropyranyl ether, 3-bromopropanol, 4-bromo-1-butanol, 3-chloropropanol, 4-chloro-1-butanol, ethylene oxide, N,N-dimethyl-N-(2-chloroethyl)-amine, 2-bromoethylamine and N,N-dimethyl-N-(3-chloropropyl)-amine.

The compounds of the formula (3) can be used as dye-bleach catalysts in a processing bath, preferably the acid dye-bleaching bath, which, if desired, can be combined with the silver bleaching bath, and/or in a layer of the photographic silver dye-bleach material.

They are particularly readily soluble in acid baths and have an excellent action as dye-bleach catalysts.

They can be used either on their own or in the presence of other conventional dye-bleach catalysts.

It is also possible for different compounds of the formula (3) to be employed at the same time in the dye bleaching bath and/or the silver bleaching bath. Finally, the compounds of the formula (3) can also be employed in conjunction with other bleach-promoting measures, for example by adding organic solvents or bleaching accelerators to the bleaching baths.

The present invention thus also relates to the photographic processing baths, especially the dye-bleaching baths, the silver bleaching baths or the combined dye-bleaching and silver bleaching baths for the silver dye-bleach process, which contain, as bleach catalysts, at least one cinnoline or pyridazine of the formula (3).

The amount in which the bleach catalysts are employed in the treatment baths can vary within wide limits and is about 0.01 to 5 g/l of treatment bath.

An aqueous dye bleaching bath according to the present invention as a rule contains (a) a strong acid, (b) a silver complexing agent, such as urea, thiourea or ethylenethiourea and in particular a water-soluble iodide, for example sodium iodide or potassium iodide, if desired (d) an antioxidant, (e) a dye-bleach catalyst of the formula (3) and, if desired, (f) a bleaching accelerator, whilst the silver bleaching baths as a rule also contain a water-soluble oxidising agent (c), in addition to the said components. The combined dye bleaching and silver bleaching baths (for rapid processing) usually contain components (a) to (e) and, if desired, component (f). In general, the aqueous bleaching preparations required for processing are allowed to act, on the developed material, in the form of dilute aqueous solutions which contain the said components.

However, other methods, for example use in paste form, are also conceivable. The temperature of the bath during processing (developing, dye bleaching and silver bleaching, fixing and washing) and in particular the temperature of the bleaching bath (or the bleaching baths) is in general between 20° and 90° C. and preferably between 20° and 60° C. or between 20° and 30° C. and, of course, the requisite processing time is shorter at a higher temperature than at a lower temperature. The aqueous bleaching preparation according to the present invention can also be prepared in the form of a liquid concentrate, especially an aqueous concentrate, and, because of its good stability, can be stored for a prolonged period. It is advantageous to use, for example, two liquid concentrates, of which one contains the strong acid (a) and the oxidising agent (c) and the other contains the remaining components (b), (d), (e) and, optionally, (f), it being possible to add an additional solvent, such as ethyl alcohol or propyl alcohol, ethylene glycol methyl ether or ethylene glycol ethyl ether, to the latter concentrate in order to improve the solubility, especially of component (e).

These concentrates can be diluted if desired, by dilution with water or with a mixture of water and an organic solvent.

The aqueous bleaching preparations which are used as a rule contain components (a) to (f) in the following amounts: (a) strong acid: 10 to 200 g/l, (b) silver complexing agent (water-soluble iodide): 2 to 50 g/l and preferably 5 to 25 g/l; (c) water-soluble oxidising agent: 1 to 30 g/l; (d) antioxidant: 0.5 to 10 g/l; (e) bleach catalyst: 0.01 to 5 g/l (in a combined dye bleaching and silver bleaching bath 0.5 to 5 g/l) and (f) bleaching accelerator: 1 to 5 g/l.

The concentrates of the individual components or combinations thereof, for example of component (a) and, if desired, (c) and also of components (b), (d), (e) and (f), can contain, per liter of concentrated preparation, 4 to 25 times and preferably 5 to 10 times the amount of the individual components which has been indicated above for the ready-to-use bleaching baths. As a rule, the concentrates are in liquid or paste form.

The strong acids contained in the dye bleaching and silver bleaching baths can be benzenesulfonic acid, succinic acid or preferably sulfuric acid or sulfamic acid. If desired, mixtures of these acids can also be employed. The pH value of the bleaching bath is in particular not higher than 2 and preferably not higher than 1.

The water-soluble iodides (component (b)) are as a rule alkali metal iodides, especially sodium iodide and potassium iodide. The oxidising agents (c) used are advantageously water-soluble aromatic nitro and dinitro compounds, as well as anthraquinonesulfonic acid derivatives. The use of such oxidising agents serves to influence the colour balance and the contrast in the images produced by the dye-bleach process and has been disclosed in German Pat. Specification No. 735,672, British Pat. Nos. 539,190 and 539,509 and Japanese Patent Publication No. 22,673/69.

The nitro and dinitro compounds are preferably mono- or di-nitrobenzenesulfonic acids, for example those of the formula

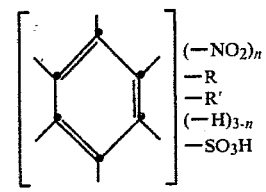

in which n is 1 or 2 and R and R' are hydrogen, lower alkyl, alkoxy, amino or halogen. The sulfonic acids can be added in the form of readily soluble salts. Suitable compounds are, for example, the sodium or potassium salts of the following acids: o-nitrobenzenesulfonic acid, m-nitrobenzenesulfonic acid, 2,4-dinitrobenzenesulfonic acid, 3,5-dinitrobenzenesulfonic acid, 3-nitro-4-chlorobenzenesulfonic acid, 2-chloro-5-nitrobenzenesulfonic acid, 4-methyl-3,5-dinitrobenzenesulfonic acid, 3-chloro-2,5-dinitrobenzenesulfonic acid, 2-amino-4-nitrobenzenesulfonic acid and 2-amino-4-nitro-5-methoxybenzenesulfonic acid.

As well as acting as silver-bleaching agents, the compounds of component (c) serve to level off the gradation.

The antioxidants (d) used are advantageously reductones or water-soluble mercapto compounds. Suitable reductones are in particular aci-reductones containing a 3-carbonyl-1,2-enediol grouping, such as reductine, triose-reductone or preferably ascorbic acid. Mercapto compounds which can be used are, for example, thioglycerol, but especially the compounds of the formulae $$HS-C_qH_{2q}-B$$

or $$HS-(CH_2)_m-COOH,$$

in which q is an integer with a value of from 2 to 12, B is a sulfonic acid group or carboxylic acid group and m is one of the numbers 3 and 4. Mercapto compounds which can be used as antioxidants are described in German Offenlegungsschrift No. 2,258,076 and in German Offenlegungsschrift No. 2,423,814. Suitable bleaching accelerators (f) are, for example, quaternary ammonium salts, such as have been disclosed in German Offenlegungsschriften Nos. 2,139,401 and 2,716,136. They are preferably quaternary, substituted or unsubstituted piperidine, piperazine, pyrazine, quinoline or pyridine compounds, the latter being preferred. Furthermore, tetraalkylammonium compounds (alkyl having 1 to 4 carbon atoms) and alkylenediammonium compounds can also be used. Specific compounds are: tetraethylammonium iodide; $(CH_3)_3N^{\oplus}(CH_2)_2N^{\oplus}(CH_3)_3.2I^{\ominus}$; $(CH_3)_3N^{\oplus}(CH_2)_6N^{\oplus}(CH_3)_3.2I^{\ominus}$, N-methylpyridinium iodide; N-methylquinolinium iodide; N-hydroxyethylpyridinium chloride; N-hydroxypropylpyridinium bromide; N-methyl-2-hydroxymethylpyridinium iodide; N,N-dimethylpiperidinium iodide; N,N'-dimethylpyrazium fluorosulfate and γ-picolinium hydrogen sulfate.

The silver fixing baths can be of known and conventional composition. The fixer used is, for example, sodium thiosulfate or, advantageously, ammonium thiosulfate if desired with additives such as sodium bisulfate and/or sodium metabisulfite.

All the baths can contain further conventional additives, such as hardeners, fluorescent brighteners and UV stabilisers.

The process for the rapid processing of silver dye-bleach materials can be used, for example, in the production of positive colour images in automatic copying or recording machines or in the rapid processing of other silver dye-bleach materials, for example for scientific recording and industrial purposes, for example coloured photofluorography.

If the bleach catalysts of the formula (3) are in a layer of the silver dye-bleach material they can be incorporated, for example, in a layer which is free from imagewise bleachable dye. The multi-layer material can thus, for example, have an additional gelatine layer which contains only the catalyst and is located directly on the layer support or between two dye layers, i.e. is adjacent to the dye layers.

In the latter case, the layer containing the catalyst also acts as an intermediate layer. Furthermore, the catalyst can also be incorporated in layers which contain colloidal silver, in filter layers (yellow filters) or in finishing layers. These filter layers, and also the layers containing the image dyes, advantageously contain gelatine as the protective colloid.

The bleach catalysts of the formula (3) can, however, also be incorporated direct in a layer containing an image dye. In other respects, the multi-layer material can have the conventional composition. Coloured photographic images can be produced in a conventional manner known per se using the photographic materials of the indicated composition.

Accordingly, the present invention also relates to a photographic material for the silver dye-bleach process, containing, on a base, in at least one layer, a compound of the formula (3) as the bleach catalyst, the bleach catalyst preferably being in the indicated layers, for example in a dye layer or in a layer adjacent to this layer.

The silver dye-bleach material used can be a transparent, metallically reflecting or preferably white-opaque material, the base of which is not able to absorb any liquid from the baths.

The base can consist, for example, of cellulose triacetate or polyester, which can be pigmented. If it consists of paper fibres, these must be lacquer-coated, or coated with polyethylene, on both sides. The light-sensitive layers are located on at least one side of this base, preferably in the known arrangement, i.e. at the bottom a red-sensitised silver halide emulsion layer, which contains a cyan azo dye, above this a green-sensitised silver halide emulsion layer, which contains a magenta azo dye, and at the top a blue-sensitive silver halide emulsion layer, which contains a yellow azo dye.

If desired, the dyes and the silver halide emulsions assigned thereto can, at least in part, be incorporated separately in adjacent layers.

The material can also contain subbing layers, intermediate layers, filter layers and protective layers, but the total thickness of the layers should as a rule not exceed 20μ.

The benzo-[c]-cinnolines which can be used according to the invention are listed in Table I and the pyrido-[c]-cinnolines are listed in Table II.

TABLE I

Benzo-[C]-cinnolines of the formula (100)

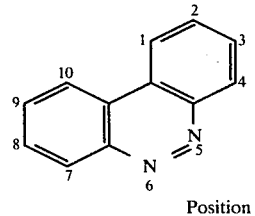

| Compound | Position | | | | | |
|----------|---|---|---|---|---|---|
| | 2 | 3 | 4 | 7 | 8 | 9 |
| 101 | H | H | H | H | H | H |
| 102 | H | CH₃ | H | H | CH₃ | H |
| 103 | H | CH₂OH | H | H | CH₂OH | H |

TABLE I-continued

Benzo-[C]-cinnolines of the formula (100)

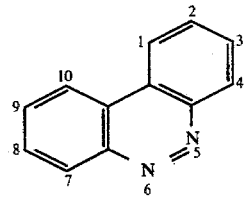

| Compound | 2 | 3 | 4 | 7 | 8 | 9 |
|---|---|---|---|---|---|---|
| 104 | H | SO$_3$Na | H | H | SO$_3$Na | H |
| 105 | H | CH$_2$SO$_3$Na | H | H | CH$_2$SO$_3$Na | H |
| 106 | H | CH$_3$ | H | H | H | H |
| 107 | H | CH$_2$OH | H | H | H | H |
| 108 | H | SO$_3$Na | H | H | H | H |
| 109 | H | CH$_2$SO$_3$Na | H | H | H | H |
| 110 | H | CH$_2$NH$_2$ | H | H | H | H |
| 111 | H | CH$_2$NH$_2$ | H | H | CH$_2$NH$_2$ | H |
| 112 | H | CH$_2$N(CH$_3$)$_2$ | H | H | CH$_2$N(CH$_3$)$_2$ | H |
| 113 | H | NH$_2$ | H | H | NH$_2$ | H |
| 114 | H | NH$_2$ | H | H | H | H |
| 115 | H | N(CH$_3$)$_2$ | H | H | H | H |
| 116 | H | N(CH$_3$)$_2$ | H | H | N(CH$_3$)$_2$ | H |
| 117 | H | OCH$_3$ | H | H | OCH$_3$ | H |
| 118 | H | OH | H | H | OH | H |
| 119 | H | OCH$_3$ | H | H | H | H |
| 120 | H | OH | H | H | H | H |
| 121 | CH$_3$ | OH | H | H | H | H |
| 122 | H | —OCH$_2$CH$_2$OH | H | H | H | H |
| 123 | H | —OCH$_2$CH$_2$OH | H | H | —OCH$_2$CH$_2$OH | H |
| 124 | H | —O(CH$_2$)$_3$OH | H | H | H | H |
| 125 | H | —O(CH$_2$)$_3$OH | H | H | —O(CH$_2$)$_3$OH | H |
| 126 | H | —O(CH$_2$)$_2$SO$_3$K | H | H | H | H |
| 127 | H | —O(CH$_2$)$_2$SO$_3$K | H | H | —O(CH$_2$)$_2$SO$_3$K | H |
| 128 | H | —O(CH$_2$)$_2$NH$_2$ | H | H | —O(CH$_2$)$_2$NH$_2$ | H |
| 129 | H | —O(CH$_2$)$_2$NH$_2$ | H | H | H | H |
| 130 | H | —O(CH$_2$)$_2$NH$_2$ | H | H | H | H |
| 131 | H | —O(CH$_2$)$_3$NH$_2$ | H | H | —O(CH$_2$)$_3$NH$_2$ | H |
| 132 | CH$_3$ | —O(CH$_2$)$_2$SO$_3$K | H | H | H | H |
| 133 | CH$_3$ | —O(CH$_2$)$_3$SO$_3$K | H | H | H | H |
| 134 | H | —O(CH$_2$)$_4$SO$_3$K | H | H | —O(CH$_2$)$_4$SO$_3$K | H |
| 135 | H | —O(CH$_2$)$_4$SO$_3$K | H | H | H | H |
| 136 | CH$_3$ | —O(CH$_2$)$_2$OH | H | H | H | H |
| 137 | CH$_3$ | —O(CH$_2$)$_3$OH | H | H | H | H |
| 138 | H | —O(CH$_2$)$_3$SO$_3$Na | H | H | H | H |
| 139 | H | —O(CH$_2$)$_3$SO$_3$Na | H | H | —O(CH$_2$)$_3$SO$_3$Na | H |
| 140 | CH$_3$ | H | H | H | H | CH$_3$ |
| 141 | CH$_3$ | H | H | H | H | H |
| 142 | CH$_2$OH | H | H | H | H | CH$_2$OH |
| 143 | NH$_2$ | H | H | H | H | H |
| 144 | N(CH$_3$)$_2$ | H | H | H | H | H |
| 145 | CH$_3$O | H | H | H | H | H |
| 146 | OH | H | H | H | H | H |
| 147 | O(CH$_2$)$_2$OH | H | H | H | H | H |
| 148 | O(CH$_2$)$_3$OH | H | H | H | H | H |
| 149 | O(CH$_2$)$_2$SO$_3$K | H | H | H | H | H |
| 150 | O(CH$_2$)$_3$SO$_3$K | H | H | H | H | H |
| 151 | O(CH$_2$)$_2$NH$_2$ | H | H | H | H | H |
| 152 | O(CH$_2$)$_4$SO$_3$K | H | H | H | H | H |
| 153 | OCH$_3$ | H | H | H | H | OCH$_3$ |
| 154 | OH | H | H | H | H | OH |
| 155 | NH$_2$ | H | H | H | H | NH$_2$ |
| 156 | N(CH$_3$)$_2$ | H | H | H | H | N(CH$_3$)$_2$ |
| 157 | CH$_2$NH$_2$ | H | H | H | H | CH$_2$NH$_2$ |
| 158 | CH$_2$NH$_2$ | H | H | H | H | H |
| 159 | CH$_2$N(CH$_3$)$_2$ | H | H | H | H | H |
| 160 | CH$_2$N(CH$_3$)$_2$ | H | H | H | H | CH$_2$N(CH$_3$)$_2$ |
| 161 | OCH$_2$CH$_2$OH | H | H | H | H | OCH$_2$CH$_2$OH |
| 162 | O(CH$_2$)$_3$OH | H | H | H | H | O(CH$_2$)$_3$OH |
| 163 | O(CH$_2$)$_2$SO$_3$Na | H | H | H | H | O(CH$_2$)$_2$SO$_3$Na |
| 164 | O(CH$_2$)$_3$SO$_3$Na | H | H | H | H | O(CH$_2$)$_3$SO$_3$Na |
| 165 | O(CH$_2$)$_4$SO$_3$Na | H | H | H | H | O(CH$_2$)$_4$SO$_3$Na |
| 166 | H | H | OH | H | H | H |
| 167 | H | H | OCH$_3$ | H | H | H |
| 168 | H | H | NH$_2$ | H | H | H |
| 169 | H | H | N(CH$_3$)$_2$ | H | H | H |
| 170 | CH$_2$OH | H | H | H | H | H |
| 171 | CH$_3$O | NH$_2$ | H | H | NH$_2$ | CH$_3$O |
| 172 | CH$_3$O | N(CH$_3$)$_2$ | H | H | N(CH$_3$)$_2$ | CH$_3$O |

TABLE I-continued

Benzo-[C]-cinnolines of the formula (100)

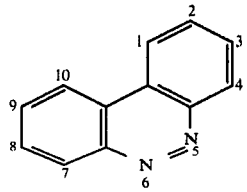

| Compound | 2 | 3 | 4 | 7 | 8 | 9 |
|---|---|---|---|---|---|---|
| 173 | $SO_3K$ | OH | H | H | H | H |
| 174 | H | $CH_2Cl$ | H | H | $CH_2Cl$ | H |
| 175 | H | $CH_2Br$ | H | H | $CH_2Br$ | H |
| 176 | $SO_3Na$ | H | H | H | H | $SO_3Na$ |
| 177 | H | $CO_2H$ | H | H | $CO_2H$ | H |
| 178 | H | $CO_2C_2H_5$ | H | H | $CO_2C_2H_5$ | H |
| 179 | H | $CO_2(CH_2)_2OCH_3$ | H | H | $CO_2(CH_2)_2OCH_3$ | H |
| 180 | H | H | OH | OH | H | H |
| 181 | H | H | $OCH_3$ | $OCH_3$ | H | H |
| 182 | H | H | $NH_2$ | $NH_2$ | H | H |
| 183 | H | H | $N(CH_3)_2$ | $N(CH_3)_2$ | H | H |
| 184 | HO | H | H | H | $OCH_3$ | H |
| 185 | H | OH | H | H | $OCH_3$ | H |
| 186 | H | $O(CH_2)_2SO_3K$ | H | H | $OCH_3$ | H |
| 187 | H | $O(CH_2)_3SO_3K$ | H | H | $OCH_3$ | H |
| 188 | H | $O(CH_2)_4SO_3K$ | H | H | $OCH_3$ | H |
| 189 | $O(CH_2)_2SO_3K$ | H | H | H | H | $OCH_3$ |
| 190 | $O(CH_2)_3SO_3K$ | H | H | H | H | $OCH_3$ |
| 191 | $O(CH_2)_4SO_3K$ | H | H | H | H | $OH_3$ |
| 192 | $OCH_3$ | H | H | H | OH | H |

Positions 1 and 10 are always occupied by hydrogen atoms.

Particularly preferred compounds are those of the formulae (101), (103), (117), (118), (120), (121), (123), (138), (153), (154) and (172) and also the compounds of the formulae (102), (104) and (113).

Table II

201 Pyrido-[5,6-c]-cinnoline
202 Pyrido-[4,5-c]-cinnoline
203 Pyrido-[3,4-c]-cinnoline
204 Pyrido-[2,3-c]-cinnoline
205 Bis-pyrido-[5,6-c;2',3'-e]-pyridazine
206 Bis-pyrido-[4,5-c;3',4'-e]-pyridazine
207 Bis-pyrido-[3,4-c;4',5'-e]-pyridazine
208 Bis-pyrido-[2,3-c;5',6'-e]-pyridazine
209 3,8-Dimethyl-bis-pyrido-[2,3-c;5',6'-e]-pyridazine In the following methods of preparation and examples, parts and percentages are by weight unless stated otherwise.

METHODS OF PREPARATION

Method of preparation 1 (compound of the formula (101))

Preparation of 2,2'-dinitrobiphenyl

According to A. I. Vogel, PRACTICAL ORGANIC CHEMISTRY; Longmans, Green and Co., London (1966), 192-193

Preparation of benzo-[c]-cinnoline

According to G. M. Badger, J. H. Seidler and B. Thompson, J. CHEM. SOC. 1951, 3,207.

Method of preparation 2 (compound of the formula (102))

(a) Preparation of 4,4'-dimethyl-2,2'-dinitrobiphenyl 180 g (0.684 mol) of 4-iodo-3-nitro-toluene are dissolved in 550 ml of N,N-dimethylformamide. The mixture is heated to 100° C. and 123 g (1.94 mols) of copper powder are then added. The mixture is then refluxed for 3 hours. The suspension is filtered hot with suction and the precipitate is washed with hot N,N-dimethylformamide. The filtrate is evaporated to dryness and the crude product is recrystallised from 500 ml of acetic acid in the presence of active charcoal.

53 g (57%) of 4,4'-dimethyl-2,2'-dinitrobiphenyl are obtained. Melting point 138°–141° C.

(b) Preparation of 3,8-dimethylbenzo-[c]-cinnoline 64 g (0.235 mol) of 4,4'-dimethyl-2,2'-dinitrobiphenyl are dissolved in 700 ml of dry toluene, under argon. 313 g (1.084 mols) of sodium dihydro-bis-(2-methoxyethoxy)-aluminate (70% in toluene) are added slowly dropwise, with stirring; an exothermic reaction takes place. The mixture is stirred for a further 10 minutes at about 80° C. The solution is evaporated to dryness. The oily residue is ground with 500 ml of water and 100 ml of concentrated ammonia. The brown suspension is filtered through a glass filter and the precipitate is washed with water. The precipitate is then extracted with ethanol in a Soxhlet apparatus for 5 days. The resulting alcoholic solution is refluxed with active charcoal and filtered hot and the filtrate is evaporated to dryness. The crude product thus obtained is finally recrystallised from a mixture of toluene/isooctane.

31 g (64%) of the compound of the formula (102) are obtained. Melting point 180°–181° C.

The nuclear magnetic resonance spectrum (in CDCl₃) confirms the indicated chemical structure of the compound.

Analysis: calculated: % C: 80.75; % H: 5.81; % N: 13.46; found: % C: 81.01; % H: 5.75; % N: 12.84.

Method of preparation 3 (compound of the formula (103))

Preparation of bis-3,8-(hydroxymethyl)-benzo-[c]-cinnoline 1.92 g (0.005 mol) of bis-(2-methoxyethyl)benzo-[c]-cinnoline-3,8-dicarboxylate (compound of the formula 179) are dissolved in 15 ml of dry toluene, under argon. 3.2 g (0.011 mol) of sodium dihydro-bis-(2-methoxyethoxy)aluminate (70% solution) are added slowly dropwise, with stirring. The mixture is heated at 60° C. for two hours. The suspension is cooled and a mixture of 100 mg of concentrated sulfuric acid, 400 mg of water and 1.1 ml of methanol is added. The resulting mixture is refluxed for one hour and then cooled. The suspension is filtered with suction, the precipitate is washed with methanol and the filtrate is evaporated to dryness. The solid residue is extracted with methylene chloride in a Soxhlet apparatus. The methylene chloride solution is concentrated and the precipitate is filtered off with suction and dried in vacuo.

0.15 g (12.5%) of the compound of the formula (103) is obtained. Melting point 240°–243° C.

The nuclear magnetic resonance spectrum (in DMSO-d6) confirms the indicated structure of the compound.

Analysis: calculated: % C: 69.99; % H: 5.04; % N: 11.66; found: % C: 68.84; % H: 5.01; % N: 11.25.

Method of preparation 4 (compound of the formula (104))

(a) Preparation of disodium 2,2'-dinitrobenzene-4,4'-disulfonate: according to J. Feldmann, Helv. 14, 764 (1931)

(b) Preparation of disodium benzo-[c]-cinnoline-3,8-disulfonate 89 g (0.15 mol) of disodium 2,2'-dinitrobenzene-4,4'-disulfonate (75.2% purity) are dissolved in a mixture of 600 ml of water and 100 ml of 30% sodium hydroxide solution. 500 mg of palladium-on-active charcoal (10%) are added and the mixture is hydrogenated under normal pressure. 18.9 l of hydrogen are absorbed. The hydrogenation mixture is heated to 80° C. and filtered hot. The solution is cooled; the product precipitates out. The precipitate is filtered off with suction and dried in vacuo at 60° C.

43.4 g (75.3%) of the compound of the formula (104) are obtained.

The nuclear magnetic resonance spectrum (in D₂O) confirms the indicated chemical structure of the compound.

Analysis: calculated: % C: 37.51; % H: 1.58; % N: 7.29; % S: 16.68; found: % C: 36.18; % H: 1.46; % N: 7.02; % S: 16.36.

Method of preparation 5 (compound of the formula (113))

(a) Preparation of 2,2'-dinitrobenzidine: according to E. Täuber, Chem. Ber. 23, 794 (1890)

(b) Preparation of 3,8-diaminobenzo-[c]-cinnoline according to F. Ullmann and P. Dieterle, Chem. Ber. 37, 23 (1904)

Method of preparation 6 (compound of the formula (117))

(a) Preparation of 4,4'-dimethoxy-2,2'-dinitrobiphenyl 335 g (1.2 mols) of 4-iodo-3-nitroanisole are dissolved in 1,000 ml of N,N-dimethylformamide. The mixture is heated to 100° C. and 229 g (3.6 mols) of copper powder are added. The mixture is refluxed for three hours. The suspension is filtered hot with suction and the precipitate is washed with hot N,N-dimethylformamide. The filtrate is evaporated to dryness and the crude product is recrystallised from a mixture of 805 ml of toluene and 580 ml of isooctane in the presence of active charcoal.

138 g (75.6%) of 4,4'-dimethoxy-2,2'-dinitrobiphenyl are obtained. Melting point 134°–137° C.

(b) Preparation of 3,8-dimethoxybenzo-[c]-cinnoline 122 g (0.4 mol) of 4,4'-dimethoxy-2,2'-dinitrobiphenyl are dissolved in 2,000 ml of absolute tetrahydrofuran, under argon. The reaction flask is cooled in an ice bath; 79.2 g (2.09 mols) of lithium aluminium hydride are then added in portions. The suspension is refluxed for a further three hours. The mixture is cooled, under argon, in an ice bath and 100 ml of water are then added slowly dropwise. The suspension is poured into 3 l of water in which 80 g of sodium hydroxide have been dissolved. The resulting mixture is heated at 70° C. for one hour. The precipitate is filtered off with suction and suspended in 3 l of 10% potassium hydroxide solution and the suspension is stirred for one hour and finally is filtered with suction. The residue is extracted with ethanol in a Soxhlet apparatus for four days. Ethanol is added to the hot extract until a clear solution forms; the suspension is refluxed over active charcoal and then filtered hot. The solution is cooled and the product precipitates out.

68 g (70.7%) of 3,8-dimethoxybenzo-[c]-cinnoline are obtained. Melting point 200°–202° C.

The nuclear magnetic resonance spectrum (in CDCl₃) confirms the indicated chemical structure of the compound.

Analysis: calculated: % C: 69.99; % H: 5.04; % N: 11.66; found: % C: 70.17; % H: 5.04; % N: 11.53.

Method of preparation 7 (compound of the formula (118))

Preparation of 3,8-dihydroxybenzo-[c]-cinnoline

A mixture of 66.4 g (0.276 mol) of 3,8-dimethoxybenzo-[c]-cinnoline (compound of the formula (117)), 550 ml of acetic acid, 275 ml of acetic anhydride and 830 ml of 43% hydrobromic acid is refluxed for 3 days. The suspension obtained after cooling the reaction mixture is poured into 5,000 ml of water. The mixture is neutralised with concentrated ammonia (to a pH value of about 6 to 7). The precipitate is filtered off with suction, washed with water and then recrystallised from 300 ml of a N,N-dimethylformamide/water mixture. The product is suspended in ethanol, filtered off with suction and dried in vacuo at 60° C.

49.3 g (84%) of 3,8-dihydroxybenzo-[c]-cinnoline are obtained.

The nuclear magnetic resonance spectrum (DMSO-d6) confirms the indicated chemical structure of the compound.

Analysis: calculated: % C: 67.93; % H: 3.81; % N: 13.21; found: % C: 67.60; % H: 3.91; % N: 13.19.

Method of preparation 8 (compound of the formula (120))

(a) Preparation of 3-hydroxybenzo-[c]-cinnoline-6-N-oxide: according to E. Waldau and R. Pütter: German Auslegeschrift No. 2,118,491.

(b) Preparation of 3-hydroxybenzo-[c]-cinnoline 10.6 g (0.05 mol) of 3-hydroxybenzo-[c]-cinnoline 6-N-oxide are dissolved in 150 ml of water and 20 ml of 30% sodium hydroxide solution. This solution is warmed to 50° C. and 13.5 g (0.07 mol) of sodium hyposulfite are added. The resulting mixture is warmed at 80° C. for 90 minutes. The solution is cooled and neutralised to a pH value of 5 to 6. A yellow-green suspension is obtained. The precipitate is filtered off with suction, washed with water and dried in vacuo at 60° C.

9.5 g (97%) of 3-hydroxybenzo-[c]-cinnoline are obtained. Melting point 274°–277° C.

The nuclear magnetic resonance spectrum (in DMSO-d6) confirms the indicated chemical structure of the compound.

Analysis: calculated: % C: 73.46; % H: 4.11; % N: 14.28; found: % C: 72.34; % H: 4.28; % N: 14.26.

Method of preparation 9 (compound of the formula (121))

Preparation of 3-hydroxy-2-methylbenzo-[c]-cinnoline (121) According to: E. Waldau and R. Pütter: German Auslegeschrift No. 2,118,491.

Method of preparation 10 (compound of the formula (123))

(a) Preparation of bis-3,8-[2-(2-tetrahydropyranyloxy)ethoxy]-benzo-[c]-cinnoline 10.6 g (0.05 mol) of 3,8-dihydroxybenzo-[c]-cinnoline (compound of the formula (118)) are dissolved in 200 ml of N,N-dimethylacetamide, under nitrogen. 5.9 g (0.0525 mol) of potassium tert.-butylate are added and the resulting red-coloured solution is warmed at 50° C. for 2 hours. 11 g (0.0525 mol) of 2-bromoethyl tetrahydropyranyl ether are added and the mixture is stirred for 3 hours at 80° C. The mixture is cooled and 5.9 g (0.0525 mol) of potassium tert.-butylate are added. The red-coloured solution is stirred for 2 hours at 50° C. 11 g (0.0525 mol) of 2-bromoethyl tetrahydropyranyl ether are added dropwise and the mixture is stirred for 3 hours at 80° C. The suspension is cooled and filtered. The filtrate is evaporated to dryness. The residue is extracted with methylene chloride. The methylene chloride solution is evaporated, the residue is ground with ether and the product is left to crystallise out. The precipitate is filtered off with suction and dried.

12.0 g (51%) of bis-3,8-[2-(2-tetrahydropyranyloxy)-ethoxy]-benzo-[c]-cinnoline are obtained. Melting point 129°–132° C.

The nuclear magnetic resonance spectrum (in CDCl3) confirms the indicated chemical structure of the compound.

Analysis: calculated: % C: 66.65; % H: 6.89; % N: 5.98; found: % C: 66.17; % H: 6.80; % N: 6.29

(b) Preparation of bis-3,8-(2-hydroxyethoxy)-benzo-[c]-cinnoline 9 g (0.0192 mol) of bis-3,8-[2-(2-tetrahydropyranyloxy)-ethoxy]-benzo-[c]-cinnoline are suspended in 75 ml of ethanol and 75 ml of water. 75 ml of concentrated hydrochloric acid are added. The mixture is heated under reflux and cooled, 200 ml of water are added and the resulting mixture is then neutralised. 4 g of sodium bisulfite are added and the suspension is warmed at 60° C. for 30 minutes. The precipitate is filtered off with suction, washed with water, dried, then ground with ether and filtered off with suction. The crude product is recrystallised from pyridine.

4.7 g (81.5%) of bis-3,8-(2-hydroxyethoxy)-benzo-[c]-cinnoline are obtained. Melting point 230°–232° C.

The nuclear magnetic resonance spectrum (in DMSO-d6) confirms the indicated chemical structure of the compound.

Analysis: calculated: % C: 64.00; % H: 5.38; % N: 9.33; found: % C: 63.58; % H: 5.33; % N: 9.04

Method of preparation 11 (compound of the formula (138))

Preparation of the potassium salt of 3-(3-sulfo-1-propoxy)-benzo-[c]-cinnoline 8.6 g (0.04 mol) of 3-hydroxybenzo-[c]-cinnoline (compound of the formula (120)) are dissolved in 80 ml of N,N-dimethylacetamide and 4.63 g (0.04 mol) of potassium tert.-butylate are added to the solution. The mixture is stirred for 15 minutes. 5.4 g (0.044 mol) of propanesultone are added and the mixture is warmed at 80° C. for 2 hours. The cooled suspension is filtered with suction. The precipitate is ground with ether, filtered off with suction and recrystallised from 120 ml of an ethanol/water mixture.

10.2 g (68%) of the potassium salt of 3-(3-sulfo-1-propoxy)-benzo-[c]-cinnoline are obtained.

The nuclear magnetic resonance spectrum (in D2O) confirms the indicated chemical structure of the compound.

Analysis: calculated: % C: 48.11; % H: 4.04; % N: 7.48; found: % C: 47.66; % H: 3.99; % N: 7.27; (with one mol of water of crystallisation)

Method of preparation 12 (compound of the formula (153))

(a) Preparation of 5,5'-dimethoxy-2,2'-dinitrobiphenyl 119 g (0.634 mol) of 3-chloro-4-nitroanisole are dissolved in 500 ml of N,N-dimethylformamide. The mixture is heated to 100° C. and 64 g (1.01 mols) of activated copper powder are added. The mixture is refluxed for four hours. A further 50 g (0.79 mol) of activated copper powder are added and the suspension is refluxed for a further 4 hours. The suspension is filtered hot, with suction, and the precipitate is washed with warm N,N-dimethylformamide. The filtrate is evaporated to dryness and the residue is ground with 1,000 ml of water, filtered off with suction and washed with water. The crude product is recrystallised from 900 ml of a toluene/isooctane mixture.

69.6 g (72.2%) of 5,5'-dimethoxy-2,2'-dinitrobiphenyl are obtained. Melting point 148°–149° C.

The nuclear magnetic resonance spectrum (in CDCl₃) confirms the indicated chemical structure of the compound.

(b) Preparation of 2,9-dimethoxy-benzo-[c]-cinnoline

This compound is prepared analogously to the compound of the formula (102), using 5,5'-dimethoxy-2,2'-dinitrobiphenyl as the starting material. The product crystallises out direct from the alcoholic extract. 2,9-Dimethoxybenzo-[c]-cinnoline is obtained in 66% yield. Melting point 170°-172° C.

The nuclear magnetic resonance spectrum (in CDCl₃) confirms the indicated chemical structure of the compound.

Analysis: calculated: % C: 69.99; % H: 5.04; % N: 11.66; found: % C: 70.19; % H: 5.02; % N: 11.45.

Method of preparation 13 (compound of the formula (154))

Preparation of 2,9-dihydroxybenzo-[c]-cinnoline

This compound is prepared analogously to the compound of the formula (118), using 2,9-dimethoxybenzo-[c]-cinnoline (compound of the formula (153)) as the starting material.

Yield: 90%.

Method of preparation 14 (compound of the formula (172))

Preparation of 3,8-diamino-2,9-dimethoxybenzo-[c]-cinnoline

According to F. Ullmann and P. Dieterle, Chem. Ber. 37, 23 (1904).

Method of preparation 15 (compound of the formula (177))

(a) Preparation of 2,2'-dinitrobiphenyl-4,4'-dicarboxylic acid

A solution of 79.2 g (0.4 mol) of 92% 4-amino-3-nitrobenzoic acid, 53.3 g (0.4 mol) of 30% sodium hydroxide solution, 30.4 g (0.44 mol) of sodium nitrite and 400 ml of water is added slowly dropwise, at about 5° C., to a solution of 198 g (6.4 mols) of concentrated hydrochloric acid and 400 ml of water. The mixture is stirred for a further one hour at 5° C. The excess nitrite is decomposed with sulfamic acid. A small amount of insoluble constituents is filtered off with suction.

A second solution is prepared by mixing a solution of 57.6 g (0.83 mol) of hydroxylamine hydrochloride in 100 ml of water and 51.2 g of potassium hydroxide (91%) (0.83 mol) in 100 ml of water and a further solution of 137.3 g (0.55 mol) of copper sulfate in 400 ml of water and 243 g (1 mol) of 28% ammonia. The diazonium solution previously prepared is added slowly dropwise to this solution at about 15° C.

The mixture is stirred for a further one hour and finally is acidified with hydrochloric acid. The resulting suspension is stirred for 15 minutes and filtered with suction. The precipitate is dissolved in an alkaline solution; the free acid is precipitated with hydrochloric acid; the resulting suspension is warmed to 70° C. and filtered with suction. The precipitate is washed with water and dried in vacuo at 70° C.

39.1 g (59%) of 2,2'-dinitrobiphenyl-4,4'-di-carboxylic acid are obtained.

The nuclear magnetic resonance spectrum (in DMSO-d6) confirms the indicated chemical structure of the compound.

Analysis: calculated: % C: 50.62; % H: 2.43; % N: 8.44; found: % C: 50.05; % H: 2.48; % N: 8.43.

(b) Preparation of benzo-[c]-cinnoline-3,8-dicarboxylic acid 16.8 g (0.05 mol) of 2,2'-dinitro-biphenyl-4,4'-dicarboxylic acid are dissolved in 150 ml of water and 13.5 g (0.1 mol) of 30% sodium hydroxide solution. 100 mg of palladium-on-active charcoal (10%) and 50 mg of platinum oxide are added and the mixture is hydrogenated under normal pressure. 4.7 l of hydrogen are absorbed. The catalyst is filtered off with suction and the filtrate is rendered slightly acid. The precipitate is filtered off with suction and recrystallised from dimethylsulfoxide. 8.5 g (63.4%) of benzo-[c]-cinnoline-3,8-dicarboxylic acid are obtained.

Method of preparation 16 (compound of the formula (179))

Preparation of bis-3,8-(2-methoxyethoxycarbonyl)-benzo-[c]-cinnoline

A mixture of 6.9 g (0.026 mol) of benzo-[c]-cinnoline-3,8-dicarboxylic acid and 9.1 g (0.0436 mol) of phosphorus pentachloride in dry chlorobenzene is refluxed for 12 hours. The mixture is cooled and the precipitate which has formed is filtered off with suction. The filtrate is evaporated to dryness. 30 ml of 2-methoxyethanol are added to the residue; the mixture is refluxed for 60 minutes and finally is filtered hot. On cooling, the product precipitates out. The precipitate is filtered off with suction and dried.

5.7 g (57.7%) of bis-3,8-(2-methoxyethoxycarbonyl)-benzo-[c]-cinnoline are obtained. Melting point 153°-156° C.

The nuclear magnetic resonance spectrum (in CDCl₃) confirms the indicated chemical structure of the compound.

The other compounds listed in Table I are also prepared analogously.

Method of preparation 17 (compound of the formula (201))

According to V. N. R. Pillai and E. Purnshathaman, CURRENT SCIENCE 46, 381 (1977)

Method of preparation 18 (compound 208)

Pyrido-[5,6-c]-cinnoline (a) Preparation of 6,6'-dinitro-2,2'-bipyridyl 50 g (0.315 mol) of 2-chloro-3-nitropyridine are dissolved in 260 ml of N,N-dimethylformamide. The solution is heated to 110° C. and 40 g (0.63 mol) of activated copper powder are added. The mixture is refluxed for two hours. A further 20 g (0.31 mol) of activated copper powder are added and the mixture is refluxed for a further 2 hours. The resulting suspension is then poured into 1,000 g of ice-water; 90 g of sodium thiosulfate are added and the resulting suspension is stirred for 60 minutes and finally is filtered with suction. The solid residue is extracted for 12 hours with 2-methoxyethanol in a Soxhlet apparatus; active charcoal is added to the extract and the mixture is refluxed and filtered hot. On concentrating and cooling the filtrate, the product precipitates out. The precipitate is filtered off with suction and dried.

not been spectrally sensitised. The following dyes are used:

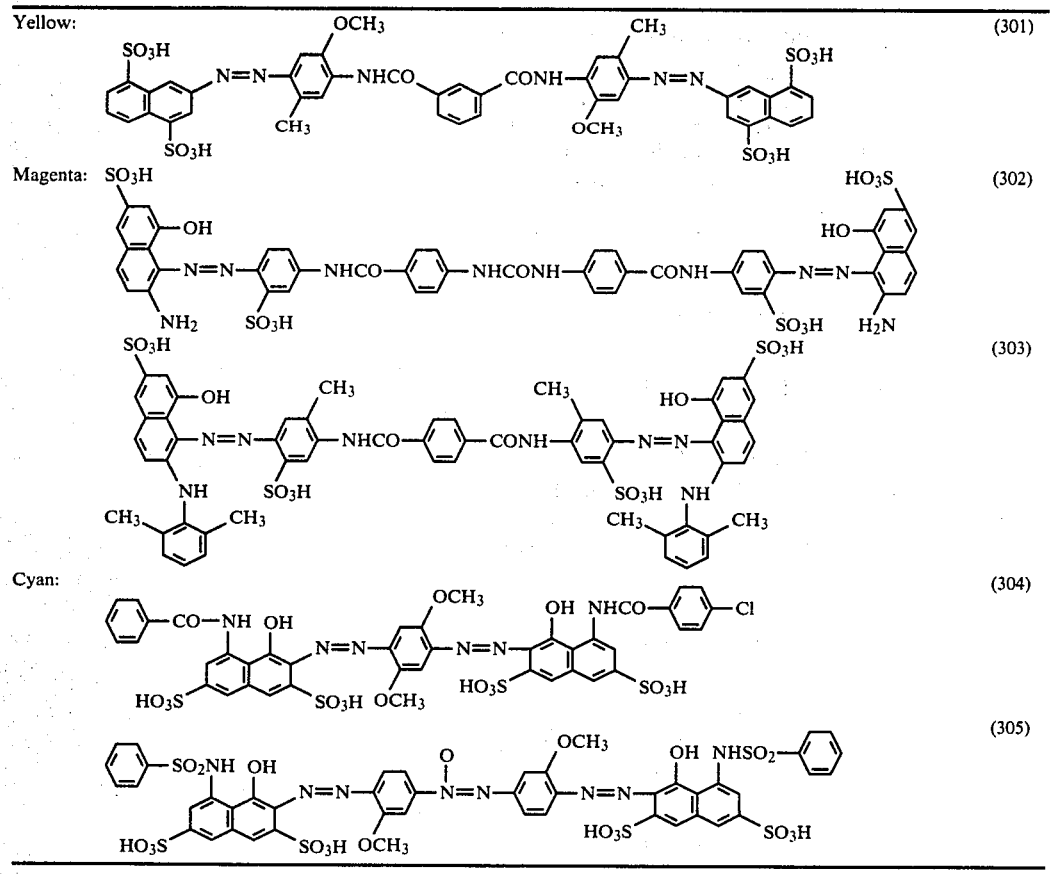

13.4 g (34.6%) of 6,6'-dinitro-2,2'-bipyridyl are obtained.

Melting point: 206°–207° C.

(b) Preparation of bis-pyrido-[2,3-c;5',6'-e]-pyridazine 10.3 g (0.042 mol) of 6,6'-dinitro-2,2'-bipyridyl and 4.2 g of sodium hydroxide are suspended in 100 ml of water. 22.7 g of sodium sulfide nonahydrate are added and the mixture is refluxed for 15 minutes. The resulting solution is extracted for 12 hours with chloroform. The chloroform solution is dried over magnesium sulfate and evaporated to dryness. The solid residue is recrystallised from isopropanol.

6.1 g (80%) of bis-pyrido-[2,3-c,5'6'-e]-pyridazine are obtained.

Melting point: 232°–233° C.

The nuclear magnetic resonance spectrum (in CDCl$_3$) confirms the indicated chemical structure of the compound.

Analysis: calculated: % C: 65.93; % H: 3.32; % N: 30.76; found: % C: 65.53; % H: 3.27; % N: 30.53.

USE EXAMPLES

The effectiveness of the benzo-[c]-cinnolines as silver dye-bleach catalysts is examined with the aid of single layer coatings of the following composition:

8.2 g of gelatine/m$^2$

Molar ratio of silver to dye: 44 to 1

Maximum transmittence density of the dye: about 1.4.

The silver halide emulsion used is a bromide/iodide emulsion which contains 2.6 mol % of iodine and has Coatings, corresponding to the above data, on opaque triacetate film are exposed behind a step wedge and then processed at 24° C. as follows:

| | |
|---|---|
| Developing bath | 6 minutes |
| Washing | 4 minutes |
| Dye bleaching bath | 7 minutes |
| Washing | 2 minutes |
| Silver bleaching bath | 2 minutes |
| Washing | 2 minutes |
| Fixing bath | 8 minutes |
| Washing | 6 minutes |
| Drying | |

A conventional black-and-white developer is used in the developing bath and baths of conventional composition are also used as the silver bleaching bath and the fixing bath. The dye bleaching bath contains the following components per liter of solution: 60 g of sulfamic acid, 0.8 ml of γ-mercapto-butyric acid, 25 g of potassium iodide and 0.35 mmol of the dye-bleach catalyst of the formula (153).

As a result of processing, a sharp yellow or magenta or cyan step wedge is obtained, depending on the dye. Similar results are also obtained with the other catalysts indicated in Tables 1 and 2.

EXAMPLE 2

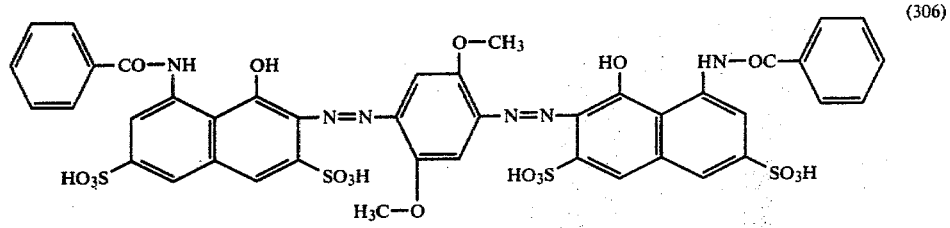

Single layer coatings according to Example 1 are exposed behind a step wedge and then processed at 24° C. as follows:

| | |
|---|---|
| Developing bath | 6 minutes |
| Washing | 4 minutes |
| Dye bleaching bath | 7 minutes |
| Washing | 2 minutes |
| Silver bleaching bath | 2 minutes |
| Washing | 2 minutes |
| Fixing bath | 8 minutes |
| Washing | 6 minutes |
| Drying | |

A conventional black-and-white developer is used in the developing bath and baths of conventional composition are also used as the silver bleaching bath and the fixing bath. The dye bleaching batch contains the following components per liter of solution: 135 g of sulfamic acid, 20 g of succinic acid, 0.5 mmol of the dye-bleach catalyst of the formula (117), 22 g of ethylenethiourea and 3 g of thiourea.

As a result of processing, a sharp yellow or magenta or cyan step wedge is obtained, depending on the dye. Similar results are also obtained with the other catalysts indicated in Tables I and II.

EXAMPLE 3

Single layer coatings according to Example 1 are exposed behind a step wedge and then processed at 24° C. as follows:

| | |
|---|---|
| Developing bath | 6 minutes |
| Washing | 4 minutes |
| Bleaching bath | 6 minutes |
| Washing | 2 minutes |
| Fixing bath | 8 minutes |
| Washing | 6 minutes |
| Drying | |

A conventional black-and-white developer is used in the developing bath and the fixing bath is a conventional fixing bath. The combined dye bleaching and silver bleaching bath contains the following components per liter of solution: 28 ml of concentrated sulfuric acid, 1 ml of thioglycerol, 9 g of sodium iodide, 10 mmols of m-nitrobenzenesulfonic acid and 2.5 mmols of the catalyst of the formula (118).

As a result of processing, a sharp yellow or magenta or cyan step wedge is obtained, depending on the dye. Analogous results are also obtained with other combinations of the catalysts listed in Tables I and II.

EXAMPLE 4

A photographic material with three dyed layers for the silver dye-bleach process is prepared on a cellulose acetate base; it contains, in the lowest, red-sensitive layer, the cyan image dye of the formula in the green-sensitive layer, above the preceding layer, the magenta image dye of the formula (302) and in the uppermost, blue-sensitive layer, the yellow image dye of the formula (301).

The image dyes are incorporated in the emulsions so as to give a reflectance density of D=2.0. The dyed layers, containing a total of 0.89 g of Ag/m$^2$, are separated by gelatine layers; the total thickness is 15μ.

This material is exposed behind a step wedge and then processed as follows:

| | |
|---|---|
| 1. Silver developing bath | |
| sodium polyphosphate | 2 g/l |
| anhydrous sodium sulfite | 50 g/l |
| hydroquinone | 6 g/l |
| sodium metaborate | 15 g/l |
| borax | 15 g/l |
| 1-phenyl-3-pyrazolidinone | 0.25 g/l |
| potassium bromide | 1 g/l |
| benztriazole | 0.1 g/l |
| 2. Bleaching bath | |
| 96% sulfuric acid | 28 ml/l |
| thioglycerol | 1 ml/l |
| sodium iodide | 9 g |
| m-nitrobenzenesulfonic acid | 5 g/l |
| catalyst : compound of the formula(138) | 1.0 g/l |
| 3. Fixing bath | |
| 60% ammonium thiosulfate | 315 ml/l |
| 60% ammonium bisulfite | 46 ml/l |
| 25% ammonia | 20 ml/l |
| 4. Washing | |

After drying, a clear neutral grey image of the subject used is obtained, the exposed regions having been bleached to pure white. Similar results are obtained when the other catalysts listed in Tables I and II are used.

What is claimed is:

1. A process for the production of coloured photographic images by the silver dye-bleach process by imagewise exposure and subsequent processing by developing the silver image, dye-bleaching and silver bleaching, optionally the last two steps can be combined, silver fixing and washing, which comprises carrying out dye-bleaching and/or silver bleaching in the presence of at least one bleach catalyst of the formula

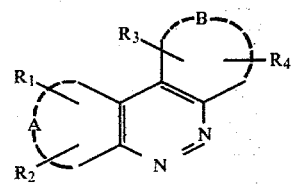

in which A and B are in each case the non-metallic atoms necessary to complete a benzene or pyridine ring, $R_1$ and $R_3$ are each hydrogen, hydroxyl, halogen, alkyl or alkoxy, each having 1 to 4 carbon atoms, carboxyl, carbalkoxy or carbalkoxyalkoxy each having 1 to 4 carbon atoms per alkoxy moiety, —CH$_2$OH, —O(CH$_2$)$_n$OH, —O(CH$_2$)$_2$O(CH$_2$)$_2$OH, —CH$_2$Cl, —CH$_2$Br, —NR$_5$R$_6$, —CH$_2$NR$_5$R$_6$, —O(CH$_2$)$_n$NR$_5$R$_6$, —CH$_2$SO$_3$M, —O(CH$_2$)$_n$SO$_3$M or —SO$_3$M, $R_2$ and $R_4$ are each hydrogen, hydroxyl or alkyl or alkoxy, each having 1 to 4 carbon atoms, and $R_5$ and $R_6$ are each hydrogen or alkyl having 1 to 4 carbon atoms, M is hydrogen, an alkali metal, ammonium or alkyl-ammonium having 1 to 4 carbon atoms per alkyl radical and n is an integer from 2 to 4.

2. A process according to claim 1, wherein $R_1$ and $R_3$ are each hydrogen, hydroxy, methyl, ethyl, methoxy, ethoxy, —CH$_2$OH, —O(CH$_2$)$_n$OH, —CH$_2$Cl, —CH$_2$Br, —CH$_2$NR$_6$R$_7$, —O(CH$_2$)$_n$NR$_6$R$_7$, —CH$_2$SO$_3$M, —O(CH$_2$)$_n$SO$_3$M, —SO$_3$M or —NR$_6$R$_7$, $R_2$ and $R_4$ are each hydrogen, hydroxyl, methyl, ethyl, methoxy or ethoxy and $R_6$ and $R_7$ are each hydrogen, methyl or ethyl and A, B, M and n are as defined in claim 1.

3. A process according to claim 2, wherein $R_1$ and $R_3$ are each hydrogen, hydroxyl, methyl, methoxy, —CH$_2$OH, —O(CH$_2$)$_n$OH, —CH$_2$NR$_8$R$_9$, —O(CH$_2$)$_n$NR$_8$R$_9$, —NR$_8$R$_9$, —SO$_3$M, —CH$_2$SO$_3$M or —O(CH$_2$)$_n$SO$_3$M, $R_2$ and $R_4$ are each hydrogen, hydroxyl, methyl or methoxy and $R_8$ and $R_9$ are each hydrogen or methyl and A, B, M and n are as defined in claim 2.

4. A process according to claim 1, wherein the bleach catalyst has the formula

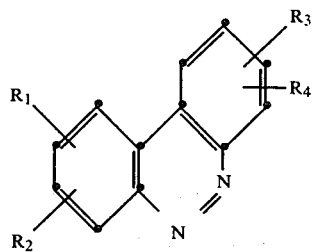

in which $R_1$, $R_2$, $R_3$ and $R_4$ are as defined in claim 1.

5. A process according to claim 4, wherein the bleach catalyst has the formula

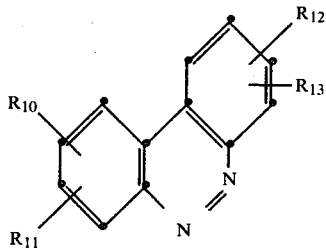

in which $R_{10}$ and $R_{12}$ are each hydrogen, hydroxyl, methyl, methoxy, hydroxymethyl, —O(CH$_2$)$_2$OH, —O(CH$_2$)$_3$OH, —NH$_2$, —N(CH$_3$)$_2$, —SO$_3$M, —CH$_2$SO$_3$M or —O(CH$_2$)$_n$SO$_3$M and $R_{11}$ and $R_{13}$ are each hydrogen, hydroxyl, methyl or methoxy, n is an integer from 2 to 4 and M is hydrogen, an alkali metal, ammonium or alkylammonium having 1 to 4 carbon atoms per alkyl radical.

6. A process according to claim 5, wherein the bleach catalyst has the formula

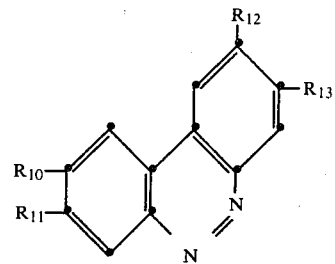

in which $R_{10}$, $R_{11}$, $R_{12}$ and $R_{13}$ are as defined in claim 5.

7. A process according to claim 5, wherein the bleach catalyst has the formula

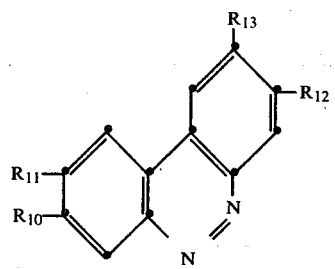

in which $R_{10}$, $R_{11}$, $R_{12}$ and $R_{13}$ are as defined in claim 5.

8. A process according to claim 5, wherein the bleach catalyst has the formula

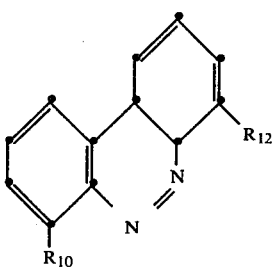

in which $R_{10}$ and $R_{12}$ are as defined in claim 5.

9. A process according to claim 1, wherein the bleach catalyst has the formula

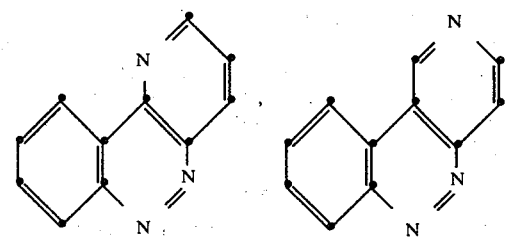

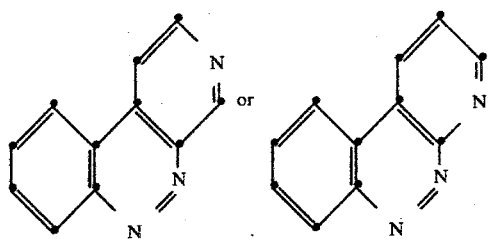

10. A process according to claim 1, wherein the bleach catalyst has the formula

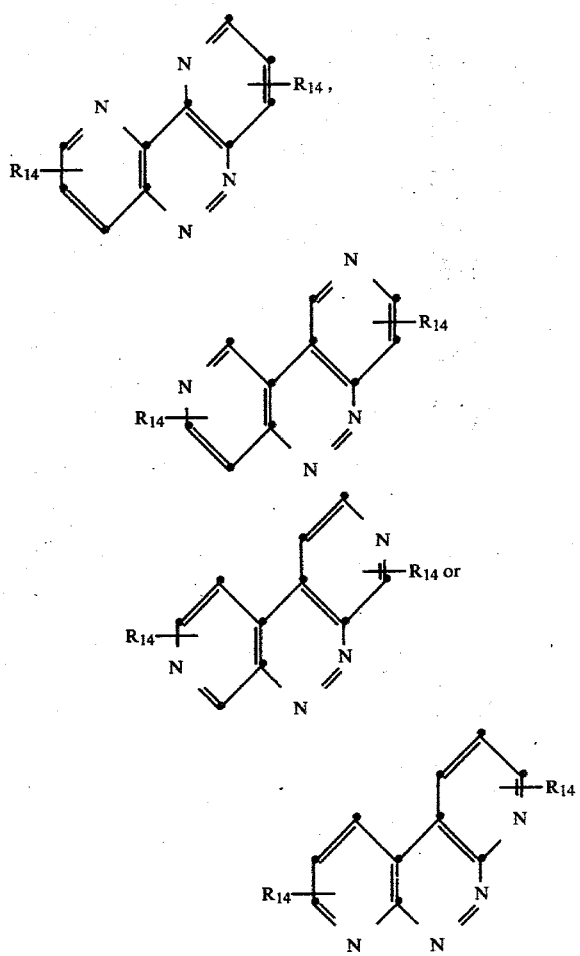

in which $R_{14}$ is hydrogen or methyl.

11. A process according to claim 1, with the processing measures silver developing, combined dye bleaching and silver bleaching, silver fixing and washing, wherein the bleaching bath used for combined dye-bleaching and silver bleaching contains (a) a strong acid, (b) a water-soluble iodide, (c) a water-soluble oxidising agent, (d) an antioxidant, (e) a bleach catalyst of the composition indicated in claim 1 and optionally (f), a bleaching accelerator and the entire processing, from silver developing to leaving the final bath, is carried out at temperatures of 20° to 90° C.

12. An aqueous preparation for combined dye-bleaching and silver bleaching, which contains (a) a strong acid, (b) a water-soluble iodide, (c) a water-soluble oxidising agent, (d) an antioxidant, (e) a bleach catalyst and, optionally desired, (f) a bleaching accelerator, wherein the bleach catalyst is a compound according to claim 1.

13. An aqueous preparation according to claim 12, which contains 0.5 to 5 g/l of the bleach catalyst.

14. An aqueous preparation according to claim 12, which is prepared from a concentrate which contains components (a) and (c) and a concentrate which contains components (b), (d), (e) and, optionally, (f), by dilution with water, which optionally can be mixed with organic solvents.

15. An aqueous preparation according to claim 12, which is in the form of separate, liquid, in particular aqueous, concentrates, of which one contains components (a) and (c) and the other contains components (b), (d), (e) and, optionally, (f).

16. An aqueous preparation for dye-bleaching, which contains (a) a strong acid, (b) a silver complexing agent, (d) if desired an antioxidant, (e) a dye-bleach catalyst and, optionally, (f) a bleaching accelerator, wherein the dye-bleach catalyst is a compound according to claim 1.

17. An aqueous preparation for silver bleaching, which contains (a) a strong acid, (b) a silver complexing agent, (c) a water-soluble oxidising agent, (d) if desired an antioxidant, (e) a bleach catalyst and, optionally, (f) a bleaching accelerator, wherein the bleach catalyst is a compound according to claim 1.

18. An aqueous preparation according to either of claims 16 and 17, which contains, optionally after dilution to the use concentrations 0.01 to 5 g/l of the bleach catalyst (e).

19. A photographic material for the silver dye-bleach process, which contains a compound according to claim 1, as the bleach catalyst, in at least one photographic layer.

20. A photographic material according to claim 19, wherein the bleach catalyst is in a dye layer or in a layer adjacent to this.

* * * * *